(12) United States Patent
Splichal

(10) Patent No.: US 12,296,107 B2
(45) Date of Patent: May 13, 2025

(54) MECHANORECEPTION STIMULATION GARMENT

(71) Applicant: NABOSO TECHNOLOGY INC., Chandler, AZ (US)

(72) Inventor: Emily Splichal, Chandler, AZ (US)

(73) Assignee: NABOSO TECHNOLOGY INC., Chandler, AZ (US)

( * ) Notice: Subject to any disclaimer, the term of this patent is extended or adjusted under 35 U.S.C. 154(b) by 17 days.

(21) Appl. No.: 17/576,668

(22) Filed: Jan. 14, 2022

(65) Prior Publication Data

US 2022/0134046 A1 May 5, 2022

Related U.S. Application Data

(63) Continuation-in-part of application No. 17/028,774, filed on Sep. 22, 2020, now Pat. No. 11,642,279,
(Continued)

(51) Int. Cl.
*A61M 21/00* (2006.01)
*A61H 39/00* (2006.01)

(52) U.S. Cl.
CPC ............. *A61M 21/00* (2013.01); *A61H 39/00* (2013.01); *A61M 2021/0022* (2013.01); *A61M 2209/088* (2013.01); *Y10T 428/24479* (2015.01)

(58) Field of Classification Search
CPC .......... A61M 21/00; A61M 2021/0022; A61M 2209/088; A61H 39/00; A61H 39/04
See application file for complete search history.

(56) References Cited

U.S. PATENT DOCUMENTS 5,551,173 A * 9/1996 Chambers ............. A43B 7/146
36/141
2014/0033565 A1 2/2014 Aruin
(Continued)

FOREIGN PATENT DOCUMENTS

JP 11131305 A * 5/1999
JP 2000271260 A * 10/2000
(Continued)

OTHER PUBLICATIONS

Translation of KR200323360Y1. (Year: 2003).*
(Continued)

*Primary Examiner* — Catherine A. Simone
(74) *Attorney, Agent, or Firm* — Womble Bond Dickinson (US) LLP

(57) ABSTRACT

A mechanoreception stimulation garment has a plurality of protuberances disposed as pyramidal nodes upon an interior surface of the fabric. The plurality of protuberances are sized, spaced apart, and arranged to target receptive fields in the glabrous innervate skin when the garment is worn. The plurality of protuberances is forced in contact with the wearer's skin when the garment is worn. The mechanoreception stimulation garment therefore increases mechanoreception, perfusion pressure, blood flow, and perception and awareness of the limb or extremity upon which the garment is worn to aid in relief of symptomology of neuropathy and, in some embodiments, assist in maintaining balance when walking or manual prehensility and dexterity in wielding objects by hand.

12 Claims, 15 Drawing Sheets

FIG. 9

Related U.S. Application Data which is a continuation of application No. 15/441,553, filed on Feb. 24, 2017, now abandoned.

(56) References Cited

U.S. PATENT DOCUMENTS

| | | | | |
|---|---|---|---|---|
| 2016/0287472 | A1* | 10/2016 | Starzhynskaya ... | A63B 21/4037 |
| 2016/0374410 | A1* | 12/2016 | Klein .................. | A41B 11/008 |
| | | | | 66/171 |
| 2017/0303635 | A1* | 10/2017 | Kazarian ............. | A43B 13/226 |

FOREIGN PATENT DOCUMENTS

| | | | | | |
|---|---|---|---|---|---|
| KR | | 200323360 Y1 * | 8/2003 | ............. | A41D 19/00 |
| WO | WO-2015135852 A1 * | | 9/2015 | ........... | A41B 11/008 |
| WO | WO-2016081482 A1 * | | 5/2016 | ........... | A41B 11/007 |

OTHER PUBLICATIONS

Translation of JP2000271260A (abstract, description and claims). (Year: 2000).*

Translation of JPH11131305A (abstract, description and claims). (Year: 1999).*

\* cited by examiner

MECHANORECEPTION STIMULATION GARMENT

BACKGROUND OF THE INVENTION

Somatosensory input from the lower limb has long been recognized as an important source of sensory information in controlling standing and balance. E.g. Paul M. Kennedy and Timothy Inglis, *Distribution and Behavior of Glabrous Cutaneous Receptors in the Human Foot Sole*, Journal of Physiology, 538.3, 995-1002 (2002). In regulating mechanoreception, cutaneous receptors in the sole of the foot are sensitive to contact pressures and may be sensitive to potential changes in distribution of pressures across receptive fields. Id. at 995.

Afferent signals from the small nerves in the plantar surface of the foot, therefore, are known to assist in balance and posture, reducing sway and regulating stride. E.g. Li Li et al., *The Contribution of Small and Large Sensory Afferents to Postural Control in Patients with Peripheral Neuropathy*, Journal of Sport and Health Science, 8, 218-227 (2019). Further, active control by nervous regulation of skeletal muscle is responsible for sway detection and postural correction. Id., 220. The functional role of the nervous system in "active control"; that is, the nervous regulation of skeletal muscle that requires energy expenditure in maintaining balance and posture; may be subdivided into four components: stimulation collection via sensory receptors, afferent signaling via sensory neurons, central nervous system ("CNS") control of information processing and decision making in the CNS, and efferent signaling to skeletal muscles via a-moto-neurons. Id.

Plantar cutaneous feedback, then, from the cutaneous receptors in the soles of the feet, help regulate postural sway and maintain balance. Id. See also Anna L. Hatton et al., *Altering Gait by Way of Stimulation of the Plantar Surface of the Foot: The Immediate Effect of Wearing Textured Insoles in Older Falters*, Journal of Foot and Ankle Research, 5, Article No. 11 (2012). Similarly, it is believed that receptors in the hands may increase profusion pressure and blood flow to the extremity, thereby heightening perception, dexterity, and prehensility.

Providing a means of stimulating the receptor fields on a user's hands and feet during stretching, for example, or stimulating the plantar receptive fields specifically when walking or standing, may greatly assist a user in walking, running, standing, and in maintaining balance and posture. Further, providing a surface material with a means of effectuating an increase in stimulation of targeted receptive fields in the user's hands and feet in proportion to the pressure applied in contact with the surface may increase stimulation in proportion with the amount of weight or force applied by the user, and thereby increasingly affect the user's balance and posture when running, for example, or when applying more weight to a particular limb, as when stretching during calisthenics, or when standing or striding on one foot, for example. Increasing stimulation of receptive fields in proportion to pressure applied in contact with the surface, therefore, may increase neuronal feedback to reflexively increase effective balance and posture and positively impact ambulation and rehabilitation in users with peripheral neuropathy as well as assist healthy users attain optimal performance.

Wheat et al. describe effects of textured socks on balance control. See "Effects of Textured Socks on Balance and Control During Single-Leg Standing in Healthy Adults," *Procedia Engineering* 72 (2014) 120-125. Prototype socks were made with nodules of 5 mm diameter that were sewn onto the sock on the plantar surface, the dorsal surface, sides of the foot, and covering the entire surface. The nodules used were craft pom-poms, sewn to the outside of the sock approximately 200 mm apart, and had relatively large diameters of 5 mm, 10 mm, and 12 mm. Id., 121.

Further, it is contemplated that increasing blood flow and perfusion pressure to the regions of the body resulting from the afferent signaling from the receptive fields may assist in rehabilitation, sensory perception, relief from symptoms of inflammation (such as arthritis, for example) and enable increased dexterity in use of the limb or extremity.

The present invention, therefore, relates to a mechanoreception stimulation garment devised to maximize mechanoreception when worn. The present invention relates to a wearable fabric item of apparel that includes an interior surface whereupon a plurality of protuberances is disposed. The interior surface therefore maintains contact with a user's glabrous innervate skin (or, in some embodiments, the hairy skin) when the garment or item of apparel is worn. Elastomeric properties of the garment may increase or force contact of the plurality of protuberances with the user's skin. Contradistinct the garments employed by Wheat et al. in their study, here the plurality of protuberances comprises a plurality of pyramidal, relatively hard (Shore A 75 in an example embodiment), polymeric structures, approximately 1.5 mm in height and with bases 2.5 mm$^2$. The bases are spaced apart not less than 1 mm and the apices are spaced apart no more than 5 mm. In a preferred embodiment configured to maximize mechanoreception from stimulation of targeted receptive fields, the apices of the nodes are spaced 3.5 mm apart. This particular grouping and arrangement of protuberances, each having an acuate apex for focused impression into the targeted receptive fields, is contemplated to maximize mechanoreception and skin perfusion pressure when forced in contact with the wearer's skin.

The garment, in all embodiments, therefore maintains stimulation of the receptive fields of a user's skin when worn by the wearer, and may assist in mechanoreception, balance and posture when walking or standing, increasing blood flow to the glabrous skin, increasing perfusion pressure at the extremities, as well as increasing awareness and to perception of the limb and the limb's position and orientation.

FIELD OF THE INVENTION

The present invention relates to a mechanoreception stimulation garment configured to stimulate the receptive fields of the wearers glabrous innervate skin to positively affect the user's balance and posture when standing and walking. The present mechanoreception stimulation garment, by maintaining pressured contact against the wearer's skin, further increases perception of the wearer's extremities as well as increasing skin perfusion pressure to lessen fatigue of the feet (when wearing the garment as a sock) and hands (when wearing the garment as a glove) and may assist in overall awareness of the limb's position and orientation thereby increasing perception of the limb, dexterity in use of the limb, and prehensility of the digits.

SUMMARY OF THE INVENTION

The present mechanoreception stimulation garment has been devised to increase mechanoreception, blood flow, and skin perfusion pressure at a limb or extremity to thereby increase balance and lessen falls (in embodiments worn on or in connection with the feet) and/or increase dexterity and prehensility (in embodiments worn on or in connection with the hands) to aid in rehabilitation of the extremity by targeted stimulation to the receptive fields in a wearer's glabrous innervate skin.

The garment herein disclosed in the detailed description and accompanying drawings is directed to a sock, or pair of socks, and, in an alternative example embodiment, as a glove, or pair of gloves. However, it is to be understood by persons of ordinary skill in the pertinent art that any such wearable garment devised to target receptive fields in the wearer's skin is intended by the present disclosure, including, for example, gloves, sweatbands, garters, undergarments, head bands, and other garments or accoutrements devised as items of apparel having an interior surface whereupon a plurality of protuberances may be disposed to contact and pressurize underlying receptive fields in the user's skin.

Such a garment presents useful improvements in the art since, configured as a garment for wear upon the body in direct contact with the skin, it maintains contact with a the skin and, where the garment exhibits some elastomeric properties, can force contact of the plurality of protuberances with the wearer's skin by action of the fabric tightening around the wearer's limb or body when worn. Further, embodiments such as socks may effectuate contact of the protuberances with the wearer's skin as a result of shoes enclosing the feet clad in the socks whereby a baseline pressure of contact is established and maintained. Inurement to such signaling is accomplished due to the pyramidal shape of the nodes comprising the plurality of protuberances whereby increased pressure, as effected by weight exerted against the limb during ambulation, for example, or in grasping or lifting or wielding an object, say, increase stimulation as more skin is stretched by increasing contact with the nodes.

It should be further noted that affixture of the plurality of protuberances to a fabric garment may comprise novelty. In an example embodiment contemplated herein, the plurality of protuberances includes polymeric nodes that have a hardness in the range of Shore A 65 to 80. Each of these nodes includes a base which is affixed to a stretchable fabric, which fabric is devised for wear as an item of apparel. The nodes are arranged in a graticulate array across an interior surface spaced and sized appropriately for directed contact with the wearer's skin in such a way as not to interfere with the general wearability and functionality of the item of apparel or garment.

In the example embodiment set forth herein, the plurality of protuberances is disposed across an interior surface of a sock in requisite position to overlie and target the wearer's receptive fields in at least the planter surface of the foot or, in another embodiment, the palmer surface of the hand. By way of example, these multi-unit innervation territories of the planter surface include fascicular receptive fields in the medial and lateral plantar nerves, and across the metatarsal-tarsal region of the foot sole. Cutaneous mechanoreceptors targeted include slow adapting type I (SAI), slow adapting type II (SAII), fast adapting type I (FAI), and fast adapting type II (FAII) receptors.

The plurality of protuberances devised herein are specifically sized and spaced apart in contemplation of maximized mechanoreception of the wearer. In an example embodiment contemplated herein, each of the plurality of protuberances is a pyramidal node, approximately 1.5 mm in height with a base of 2.5 mm$^2$. Each node is approximately 65 to 80 Shore A hardness (with a preferred hardness of 75 Shore A in at least one embodiment). The plurality of nodes may be confined to areas of the interior surface of the garment to target specific receptive fields. However, each grouping of nodes is contemplated to be no less than 1 mm apart at the base and no more than 5 mm apart at each apex, thereby confining the specific arrangement of nodes into a graticulate field to superimpose over a targeted receptive field in a wearer's glabrous innervate skin. In a preferred embodiment set forth herein, the apices of the nodes are spaced apart 3.5 mm.

The garments set forth herein, whereupon the plurality of protuberances is affixed across an interior surface, are contemplated to be socks, gloves, sweatbands, and any other item of apparel wearable upon a person in contact with the glabrous or hairy innervate skin in the hands, feet, limbs, and forehead, for example. Each of the garments is a fabric or weaved fabric representing woven fibers or other fabric construction whereby the garment is tautly wearable upon the body of a wearer. The elastomeric properties of some fabrics may increase the pressure of the protuberances' contact with the glabrous innervate skin.

The particular shape of the pyramidal nodes is devised to increase stimulation proportionately with pressure applied. Each apex of each node is relatively acuate and acute. Increasing pressured contact therewith pushes the node to stretch the user's skin upon the sides of the node. As the node slopes outwardly toward the base, so the area of skin subject to contact and stimulation is increased. This increasing stimulation proportionate to pressure applied is termed a "focus" herein throughout, the general concept being that each node stimulates a focus within the receptive field to increase afferent signaling in proportion to pressure applied. Each focus, therefore, is believed to increase mechanoreception (and thus aid in balance and in reducing sway) and also increase skin perfusion pressure to increase blood flow, lessen fatigue, and increase user perception and awareness of the extremity. In such a manner, it is contemplated that wear of the mechanoreception stimulation garment in any embodiment will increase perception and awareness of the extremity and aid in rehabilitation and alleviation of neuropathic symptomology and inflammation, such as, for example, the symptoms of arthritis in the hands. Thus, has been broadly outlined the more important features of the present mechanoreception stimulation garment so that the detailed description thereof that ii follows may be better understood and in order that the present contribution to the art may be better appreciated. Objects of the present mechanoreception stimulation garment, along with various novel features that characterize the invention are particularly pointed out in the claims forming a part of this disclosure. For better understanding of the mechanoreception stimulation garment, its operating advantages and specific objects attained by its uses, refer to the accompanying drawings and description.

BRIEF DESCRIPTION OF THE DRAWINGS

Figures

DETAILED DESCRIPTION OF THE DRAWINGS

The example embodiments illustrated in the accompanying drawings are provided for purposes of example only. Any garment capable of placing a plurality of pyramidal nodes (illustrated herein generally and not necessarily to scale) is contemplated by the present disclosure. Thus, despite the fact that an ankle sock and glove are shown in the figures herewith, it is to be understood by persons of ordinary skill in the pertinent art that the inventive disclosure set forth herein is contemplated to cover all forms of socks, gloves, sweat bands, and other such garments and/or items of apparel capable of being worn upon a user to impress a plurality of pyramidal nodes into contact with targeted receptive fields in the user's skin and to thereby stimulate afferent signaling in various nerves to increase mechanoreception, perfusion pressure, blood flow, perception, and awareness of a limb or extremity, as case may be. Thus, the mechanoreception stimulation garment 10 shown herein may be devised in any appropriate form.

Figure 1:
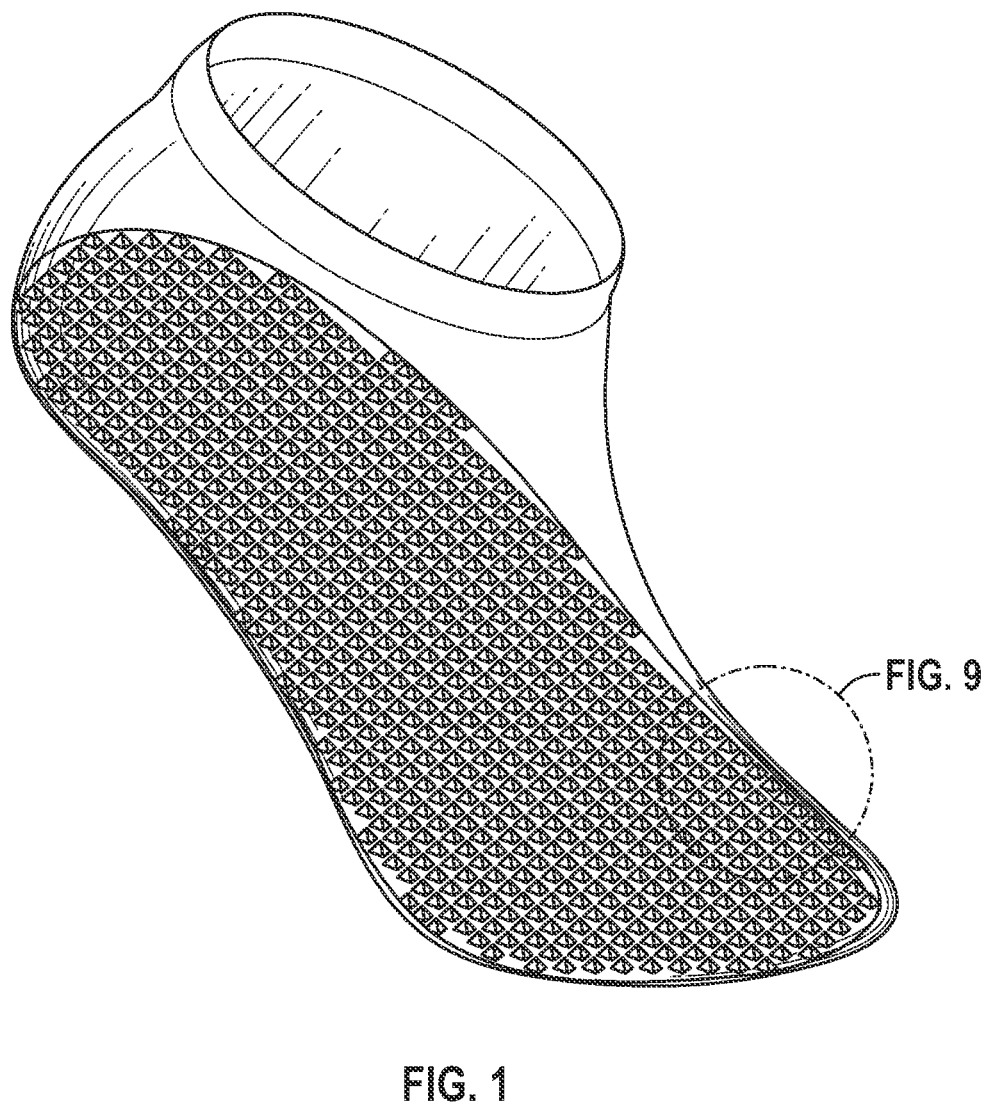
FIG. 1 is an elevation view showing the garment in the form of a sock illustrated transparently so that the plurality of pyramidal nodes upon an interior surface of the garment is rendered visible.

Discussing now generally FIG. 1, an elevation view of a mechanoreception stimulation garment 10 in the form of a sock 20 is shown with the sock 20 in outline (rendered transparently) so that an interior surface 22 of sole 24 can be seen. A plurality of protuberances 50, comprising pyramidal nodes 52, is illustrated in graticulate array up-facing across interior surface 22 of sole 24 of sock 20.

The particular pattern of protuberances 50 shown is not meant to be limiting; arrangement of the protuberances 50 in any pattern, or grouping of patterns, wherein each of the pyramidal nodes 52 is not less than 1 mm apart between bases 54 and not more than 5 mm apart between apices 56, is contemplated as within the present disclosure. In a preferred embodiment, base 54 of each of nodes 52 is not less than 1 mm apart and the apex 56 of each node 52 is approximately 3.5 mm apart.

Particular groupings of nodes 52 are contemplated as within scope of the present invention, wherein particular patterns are devised and configured to target receptive fields in the user's innervate skin. For simplicity and inclusivity in disclosure, however, the instant drawings accompanying this disclosure are shown as a plurality of protuberances 50 illustrated as a field of pyramidal nodes 52 disposed across the entire interior surface 22 upon the sole 24 of the sock 20; however, it is not intended that the field be restricted to the interior surface 22 of sole 24 of sock 20, or other garment whereupon a plurality of protuberances may be rendered for like purpose as contemplated herein.

As shown in FIG. 1, the embodiment exemplified is an ankle sock 20. The sock 20 fabric is contemplated to be stretchable to impress the plurality of protuberances 50 into the receptive fields when sock 20 is worn. Further, wearing a shoe (not shown) in conjunction with sock 20 as illustrated may further serve to impress the plurality of protuberances 50 into the targeted receptive fields. Such pressure occasioned by the sock 20 fabric, or via engagement interior to a shoe, establishes a baseline stimulation to effectuate afferent signaling from the corresponding receptive field. This baseline stimulation is accentuated when weight is placed upon the limb or when the plurality of protuberances 50 is otherwise caused to be forced in further contact with the user's innervate skin, as when grasping an object, for example, when the garment is disposed in the form of a glove worn upon the hand of the user (see, e.g., FIGS. 11-17).

It is contemplated that increased force applied to the plurality of protuberances 50 may serve to prevent inurement of the stimulation because each pyramidal node 52 impresses deeper into the innervate skin in proportion to the pressure applied. As such, an increasing area of skin is impressed and thereby accentuates corresponding afferent signaling. This increased pressure proportionately increasing afferent stimuli is referred to herein as a "focus." That is, increased pressure "focuses" afferent signaling in increasing proportion to pressure applied. Thus, inurement against generalized signaling may be prevented and focused signaling may be enhanced in-use of the garment 10.

Figures 6, 10:
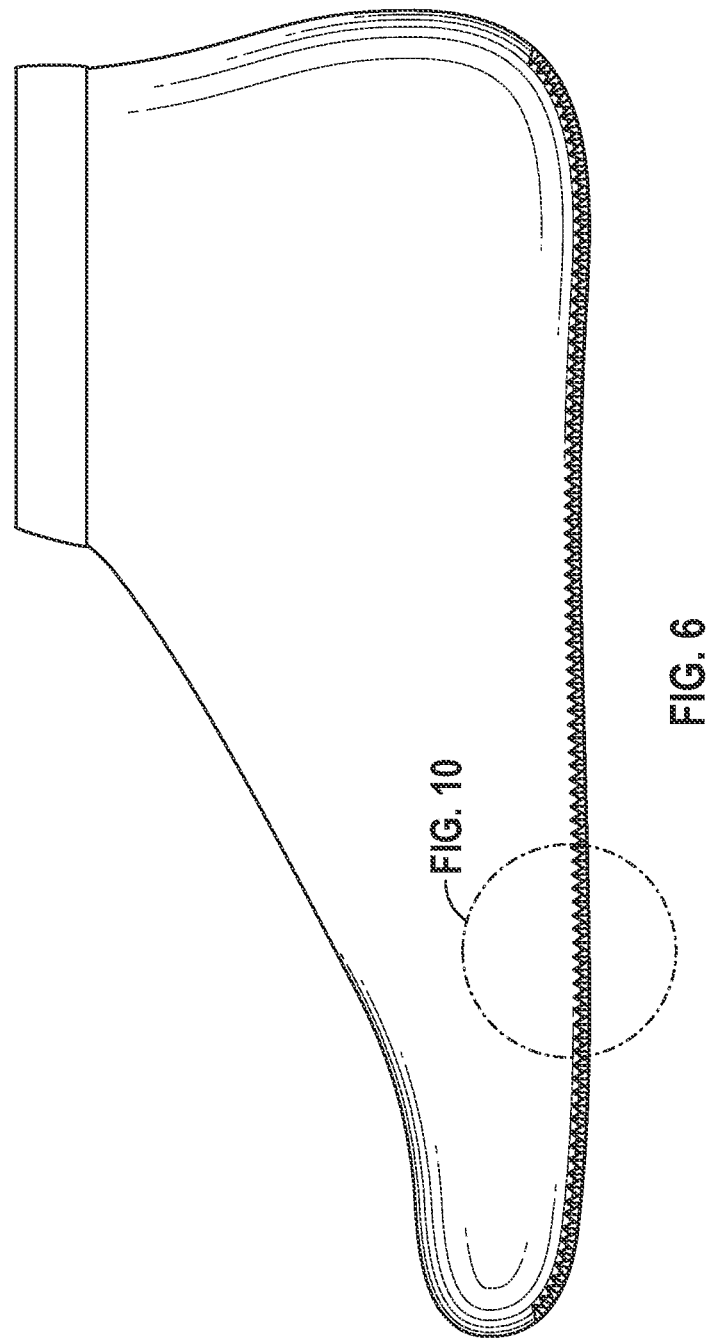
FIG. 6 is a side elevation view of the sock showing the sock transparently to render the plurality of pyramidal nodes upon the interior surface visible.
FIG. 10 is a detail view taken from the section shown in FIG. 6.
Figure 9:
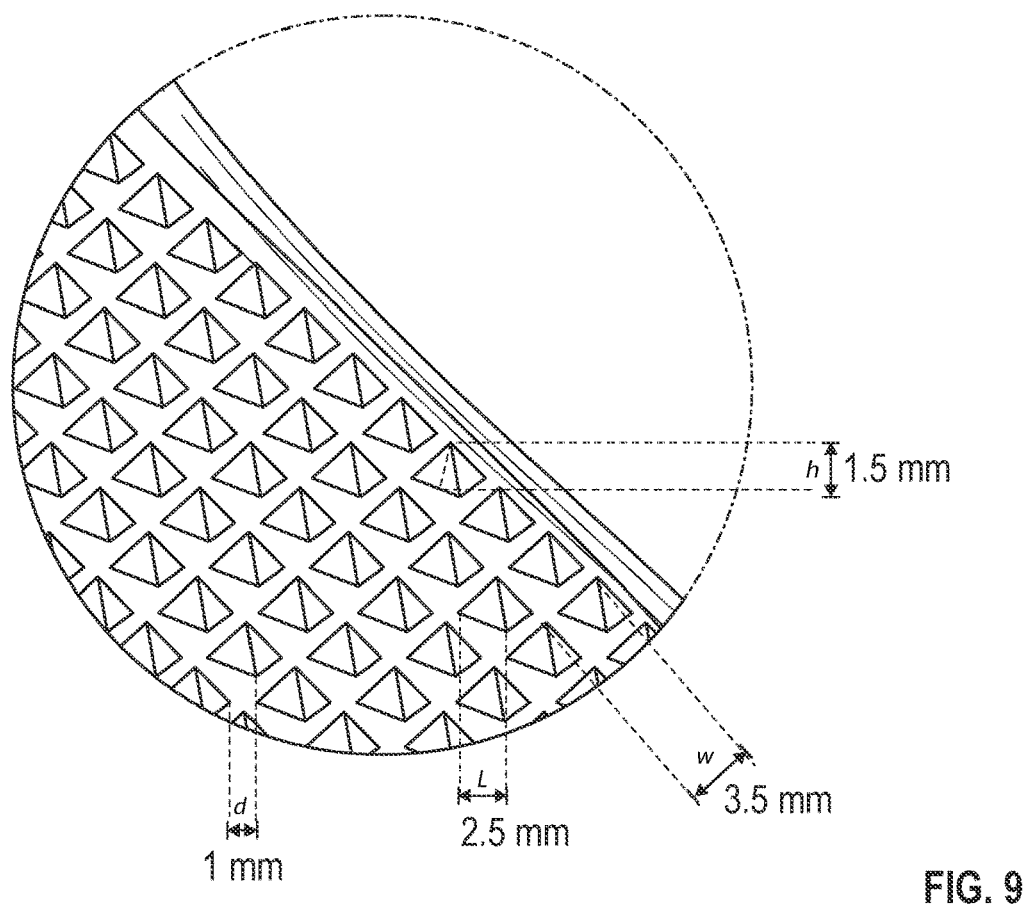
FIG. 9 is a detail view taken from the section shown in FIG. 1.
Figure 10:
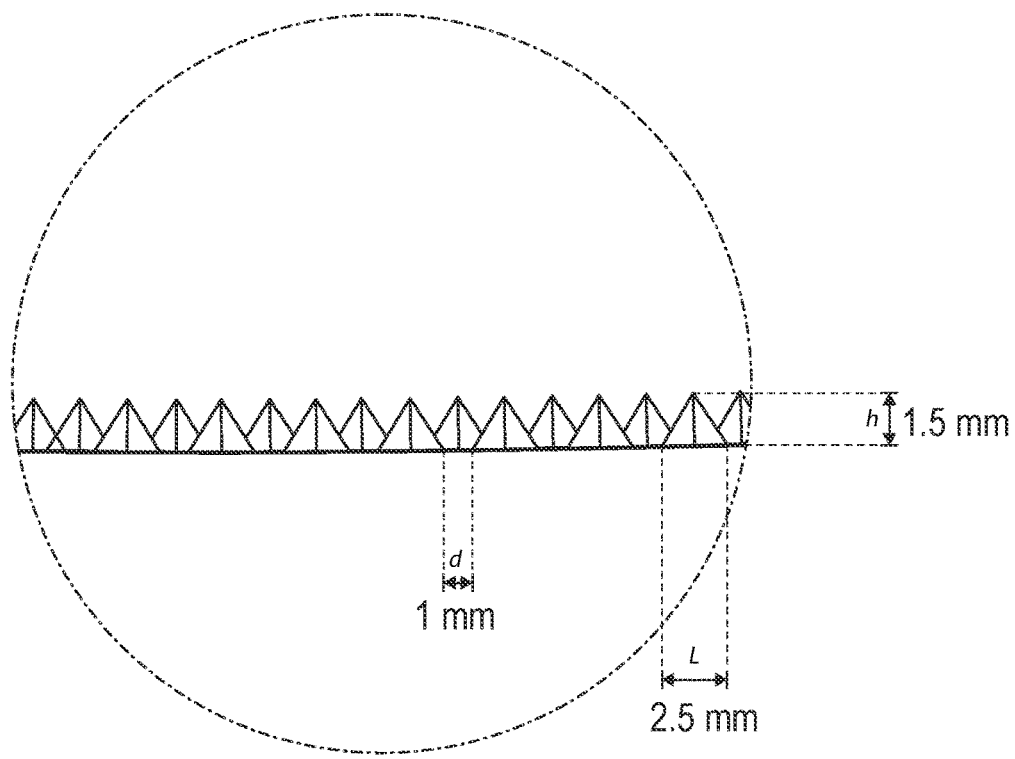

Base 54 is square and apex 56 is oriented at height h centrally above base 54 (see, e.g., detail view illustrated in FIGS. 9 and 10). In a preferred embodiment herein disclosed, height h is 1.5 mm. Base 54 has sides of L length. In the preferred embodiment herein disclosed, length L is 2.5 mm. Hardness of each node is contemplated to be between Shore A 60 and 80, with a hardness of 75 in a preferred embodiment.

As is shown in FIGS. 9 and 10, base 54 of each node 52 is disposed not less than distance d apart from adjacent bases of adjacent nodes. In the preferred embodiment herein disclosed, distance d is not less than or equal to 1 mm. Apex 56 of each node 52 is disposed not more than distance w apart from adjacent apices of adjacent nodes. In all embodiments herein disclosed, distance w is not more than 5 mm and, in the preferred embodiment, distance w is 3.5 mm.

Figure 2:
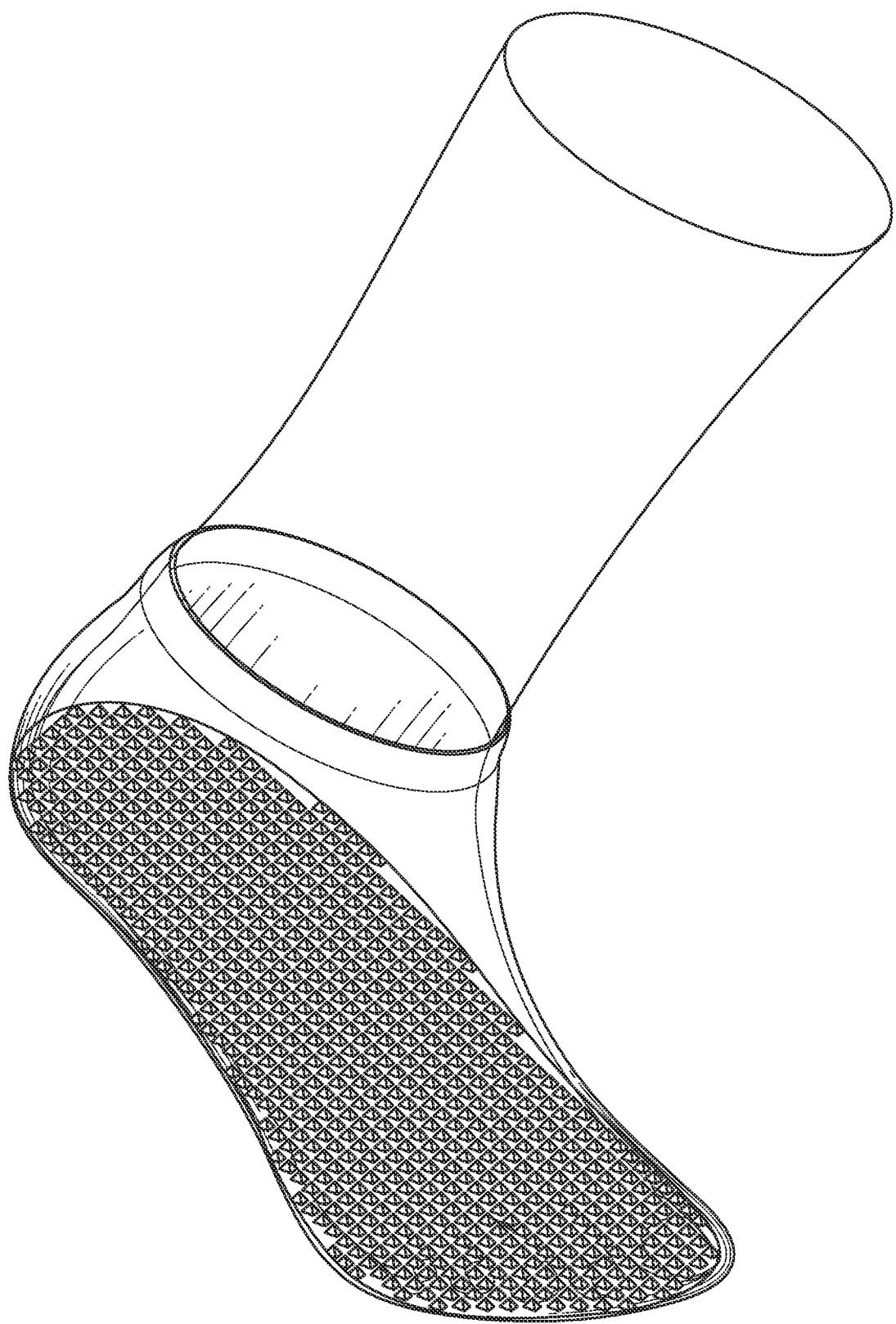
FIG. 2 is an elevation view showing the sock and a user's foot rendered transparently whereby the plurality of pyramidal nodes upon the interior surface of the garment is rendered visible.

Returning to FIG. 2, the example embodiment shown in FIG. 1 is illustrated in-use, with sock 20 and the wearer's foot being rendered transparently in order that, for the purposes of illustration, the plurality of protuberances 50 is depicted visible upon the interior surface 22 of sole 24.

Figure 3:
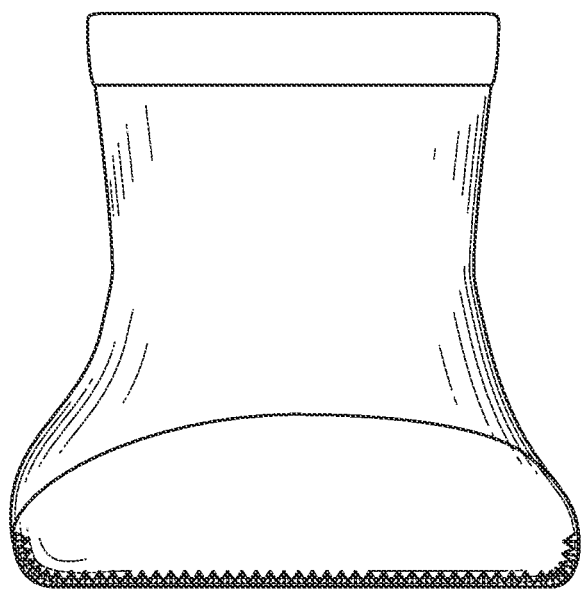
FIG. 3 is a front elevation view of the sock showing the garment transparently to render the plurality of pyramidal nodes upon the interior surface visible.
Figure 4:
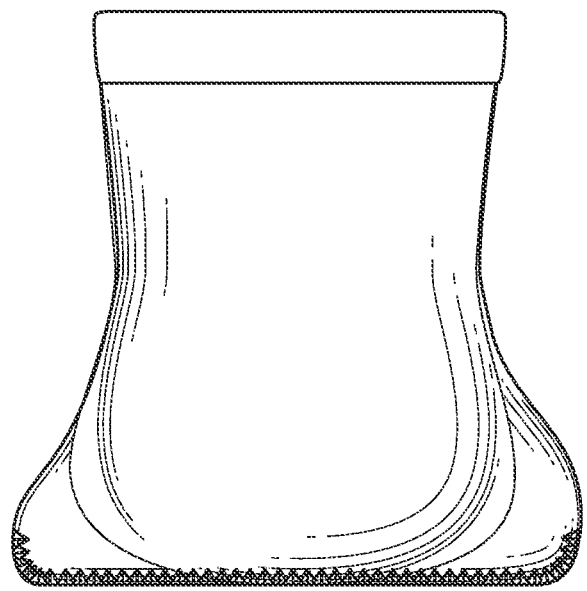
FIG. 4 is a rear elevation view of the sock showing the sock transparently to render the plurality of pyramidal nodes upon the interior surface visible.
Figure 5:
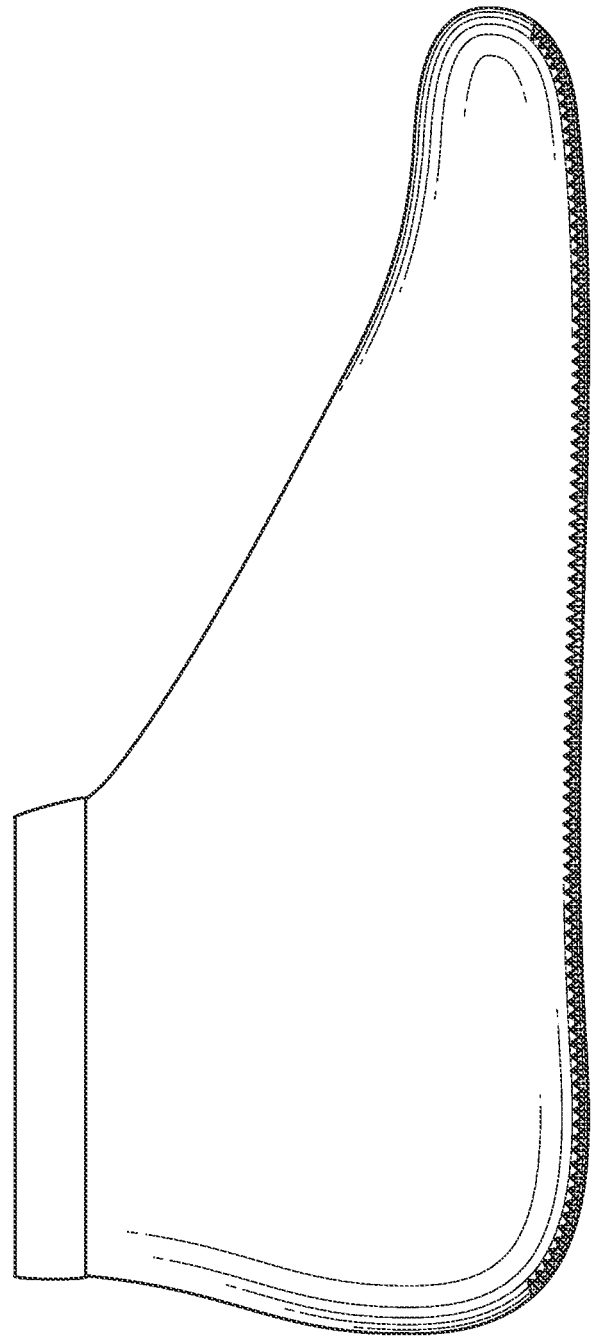
FIG. 5 is a side elevation view of the sock showing the sock transparently to render the plurality of pyramidal nodes upon the interior surface visible.
Figure 7:
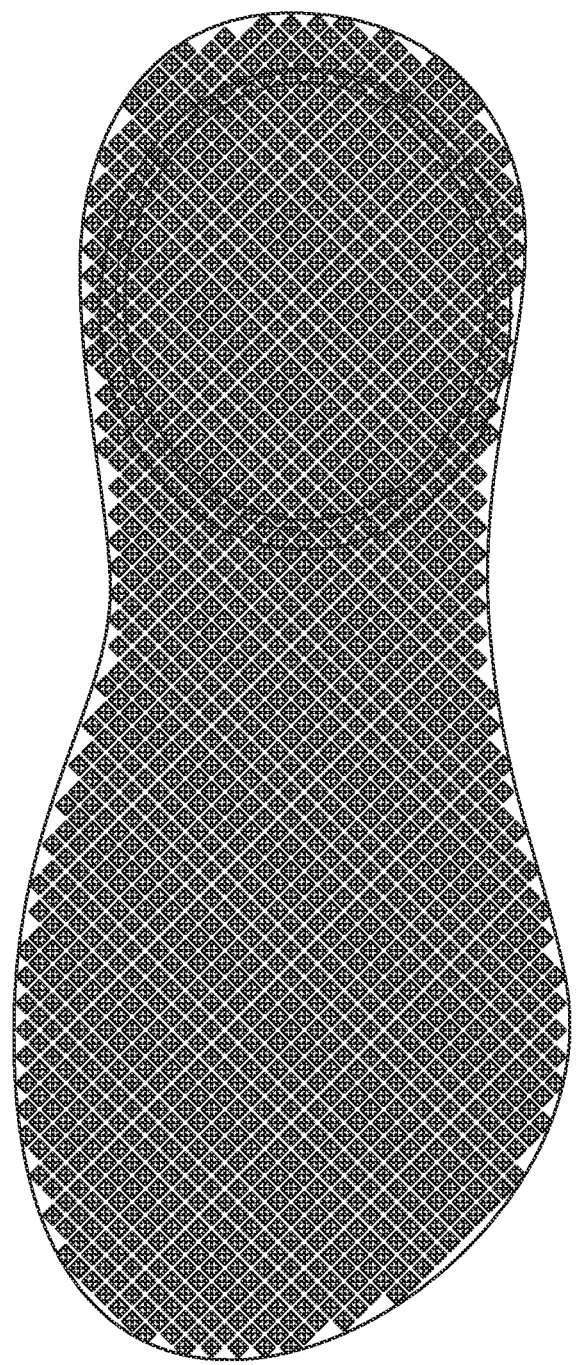
FIG. 7 is a top elevation view of the sock showing the sock transparently to render the plurality of pyramidal nodes upon the interior surface visible.
Figure 8:
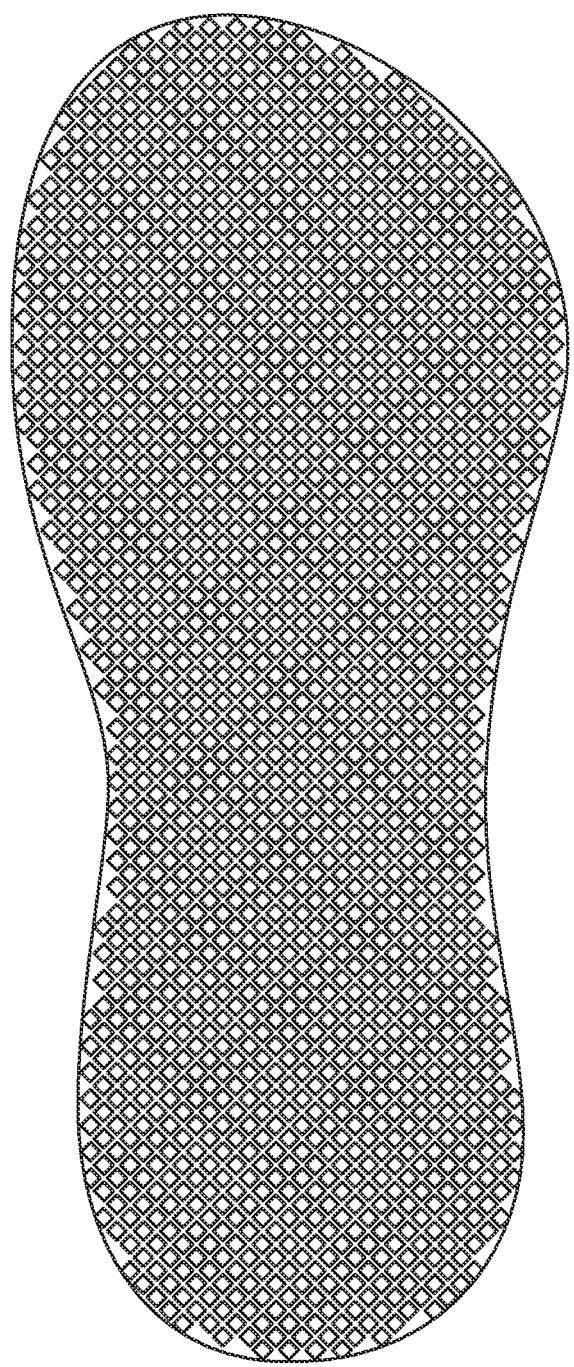
FIG. 8 is a bottom elevation view showing the sock turned inside out so that the interior surface is exposed.

FIG. 3 shows a front elevation view with sock 20 rendered transparently to show the plurality of protuberances 50 upon the interior surface 22 of sock 20 sole 24. FIG. 4 shows a rear elevation view with sock 20 rendered transparently, again to show the plurality of protuberances 50 upon the interior surface 22 of sock 20 sole 24. FIGS. 5 and 6 show side elevation views with sock 20 rendered transparently to show the plurality of protuberances 50 upon the interior surface 22 of sock 20 sole 24. FIG. 7 shows a top elevation view with sock 20 again rendered transparently to reveal the plurality of protuberances 50 upon the interior surface 22 of sock 20 sole 24. FIG. 8 is a bottom elevation view showing the garment turned inside out so that the interior surface 22 is exposed for view.

Figure 11:
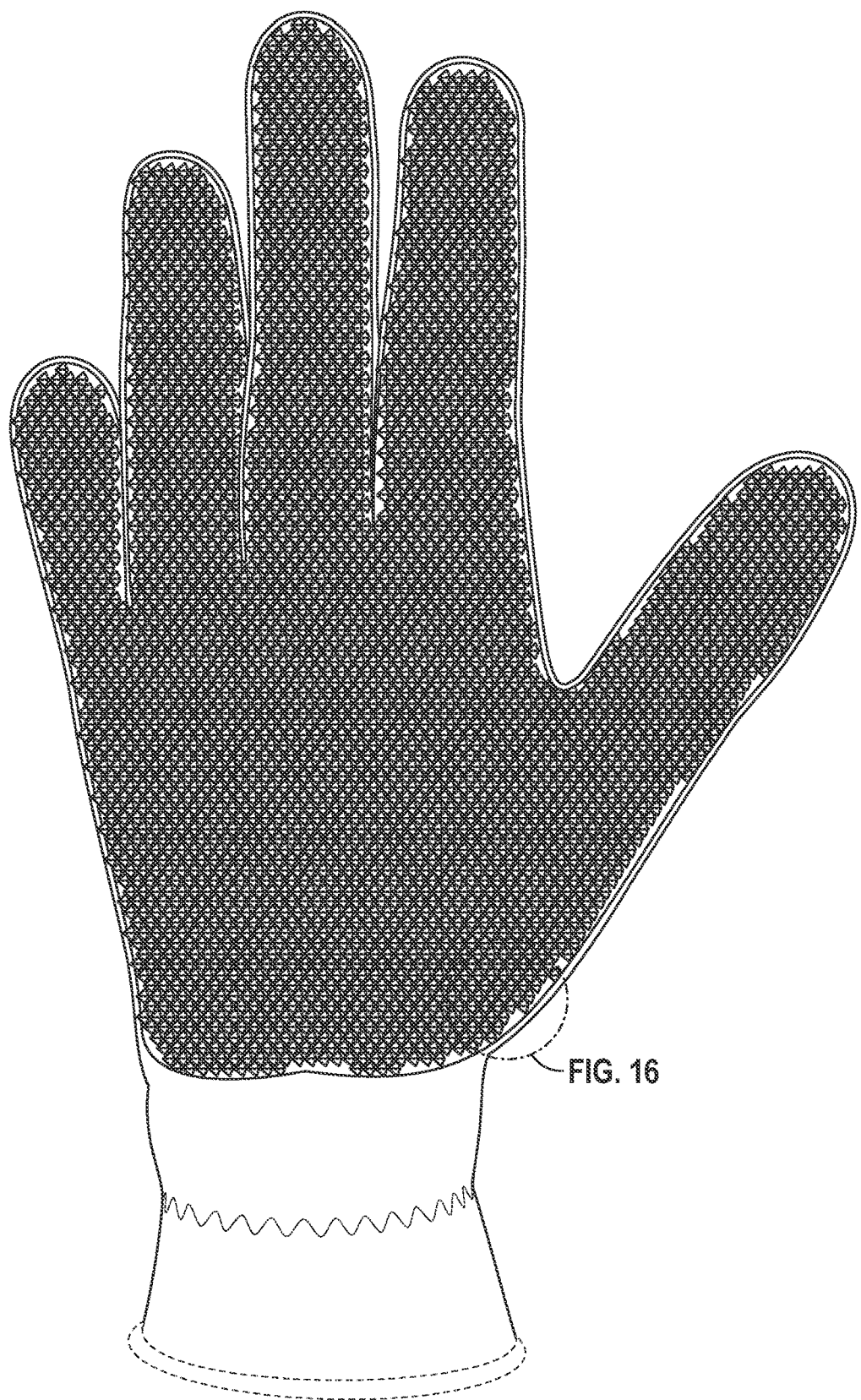
FIG. 11 is a diagonal elevation view of an example embodiment of the garment disposed in the form of a glove having the dorsal surface of the glove rendered transparently whereby the interior of the palmer surface of the glove is rendered visible for the purposes of illustration.

FIG. 11 is a diagonal elevation view of an example embodiment of the instant mechanoreception stimulation garment 10 rendered in the form of a glove 40. Plurality of protuberances 50, disposed upon the interior surface 42 of palmer surface 44 of the glove 40, is rendered visible for the purposes of illustration. The plurality of protuberances 50 is disposed to contact the innervate glabrous skin of a user's palm when the glove 40 is worn. As such, and in like manner as described above, the plurality of protuberances 50 increases mechanoreception and thus, when glove 20 is worn, aid in increasing dexterity, manipulation, and prehensility of the hand by the increased afferent signaling effectuated via stimulation of receptive fields in the hand in-use of the glove. Thus, skin perfusion pressure that increases blood flow, lessens fatigue, and increases user perception and awareness of the manual extremities, is also effectuated in-use of the glove. Increased blood flow may therefore help in lessening discomfort and pain caused by symptomology of diseases of the hand such as arthritis, for example, and assist users in prehensility and manual dexterity.

Figure 12:
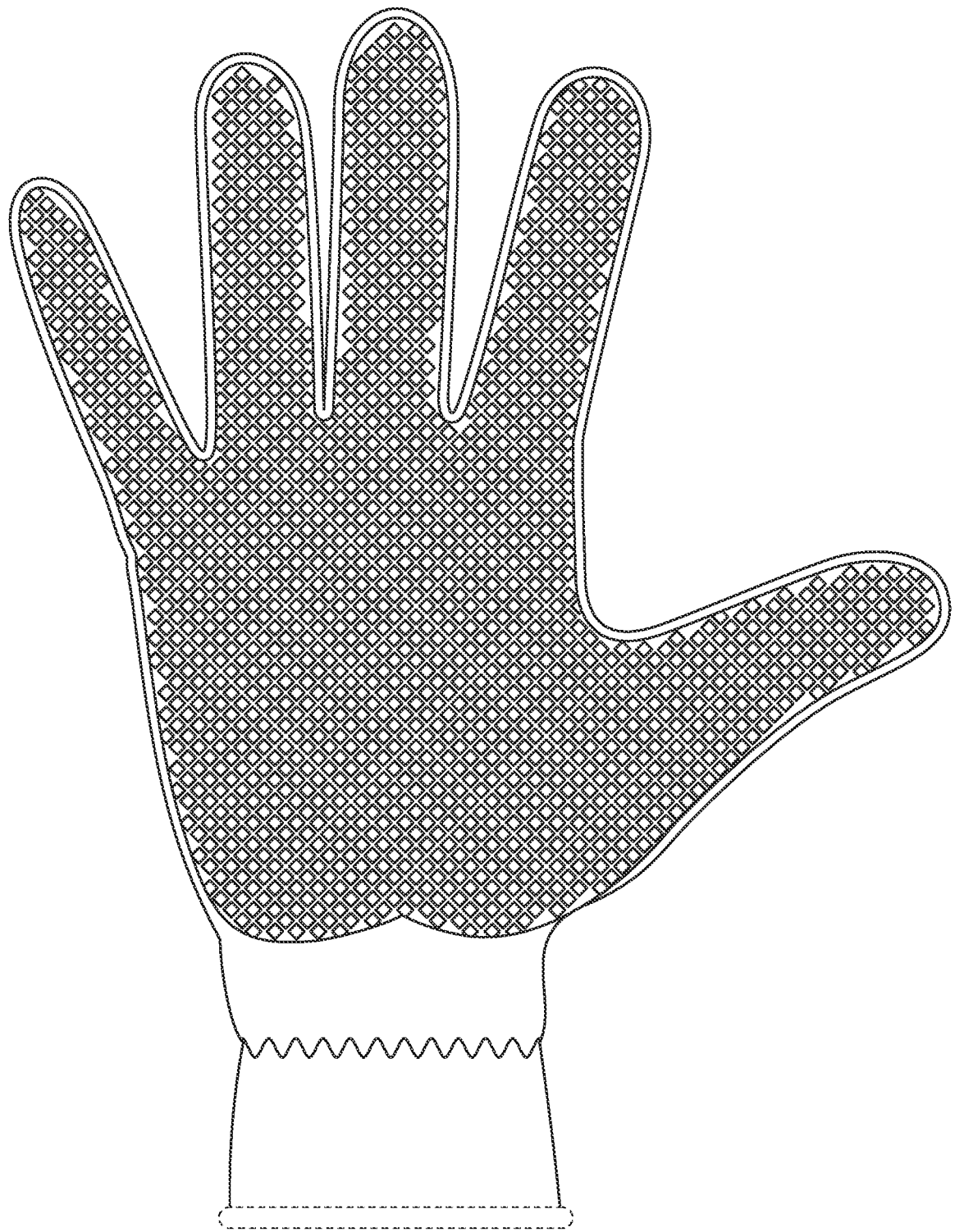
FIG. 12 is a bottom elevation view of an example embodiment of the garment disposed in the form of a glove.

FIG. 12 is a bottom elevation view of the glove 40 wherein the bases 54 of each pyramidal node 52 comprising the plurality of protuberances 50 is illustrated. Each of the nodes 52 is affixed to the fabric weave and disposed not less than 1 mm apart (see FIGS. 16 and 17). It should be noted that the continuous distribution across the interior surface 42 of the palmer surface 44 of the glove 20 is shown for the purposes of example only. Particularized distribution patterns are contemplated as within scope of this disclosure configured to directly target and stimulate specific receptive fields to maximize mechanoreception, perfusion pressure, increased blood flow, and thus awareness and manipulation of the hand.

Figure 13:
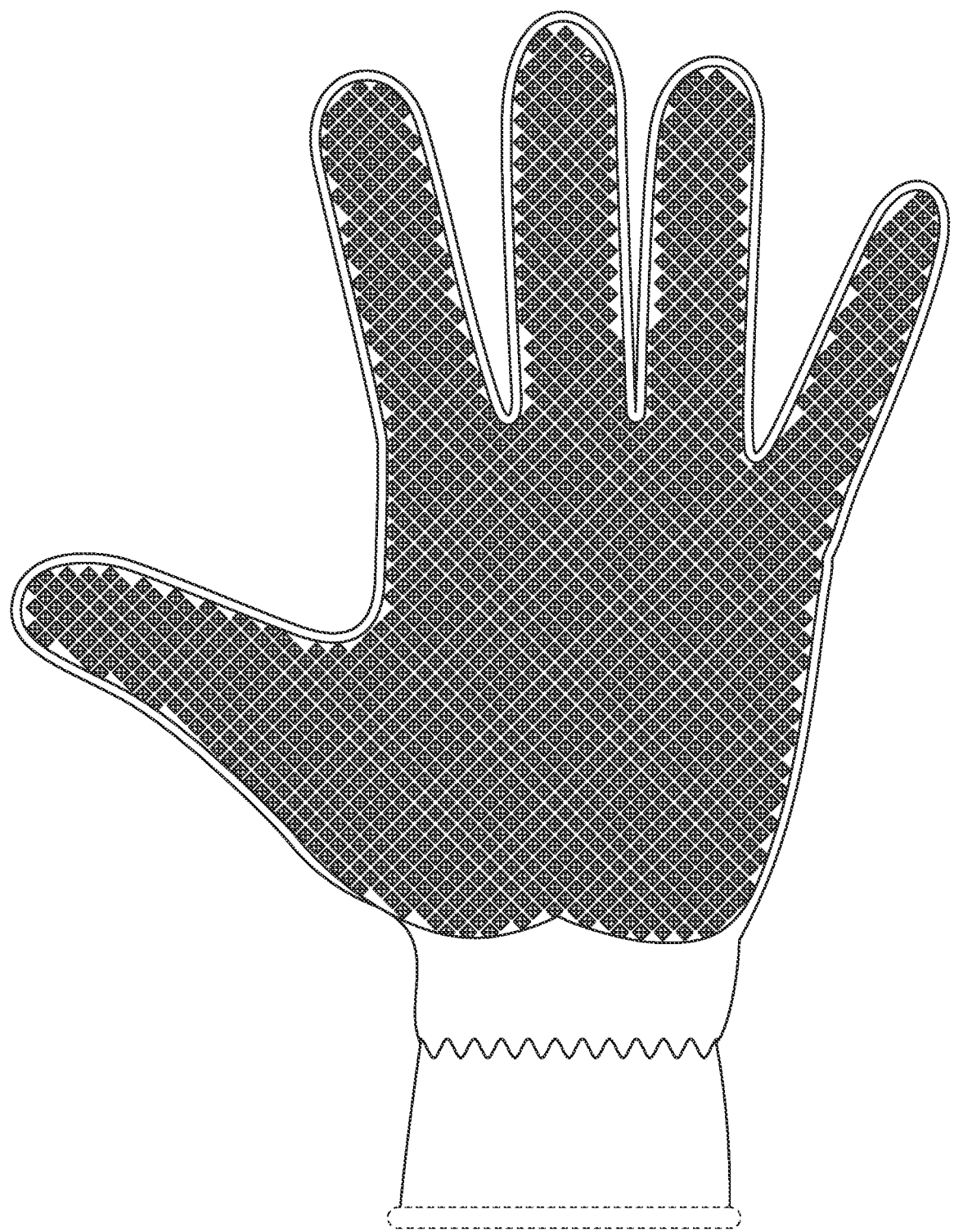
FIG. 13 is a top elevation view of an example embodiment of the garment disposed in the form of a glove for the opposite hand than the glove depicted in FIG. 11 and having the dorsal surface of the glove rendered transparently whereby the interior of the palmer surface of the glove is visible for the purposes of illustration.

FIG. 13 is a top elevation view of the glove 40 with the dorsal surface 46 of the glove 40 rendered transparently for the purposes of illustrating the plurality of protuberances 50 upon the interior surface 42 of the palmer surface 44. As mentioned above, the particular pattern and distribution of the plurality of protuberances 50 upon the interior of the palmer surface 44 of the glove 40 are shown for the purposes of example only and are not intended to be limiting. Particularized distribution patterns are contemplated as within scope of this disclosure, said patterns configured to directly target and stimulate specific receptive fields to maximize mechanoreception, perfusion pressure, increased blood flow.

Figure 14:
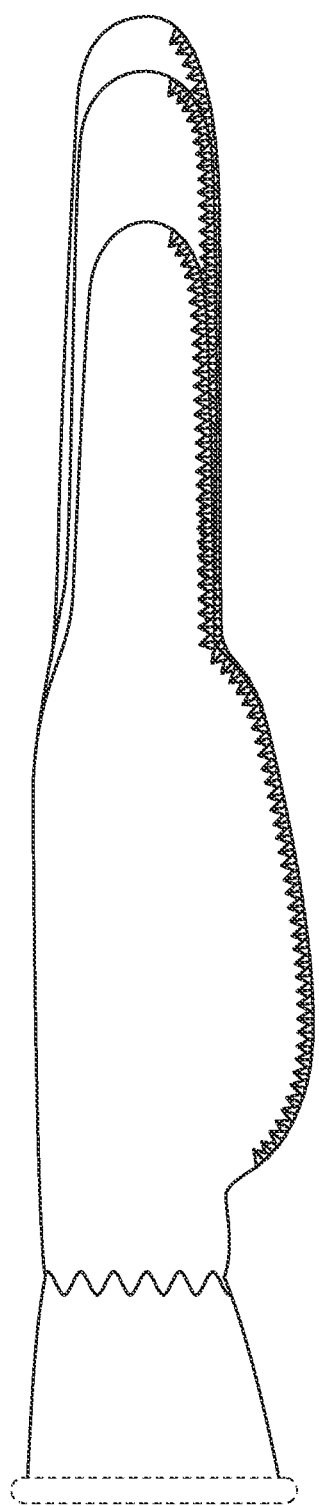
FIG. 14 is an ulnar side elevation view of an example embodiment of the garment disposed in the form of a glove with side surface rendered transparently to render the interior of the palmer surface of the glove visible for the purposes of illustration.

FIG. 14 is an ulnar side elevation view of the glove 40 with the glove 40 rendered transparently for the purposes of illustration of the plurality of protuberances disposed upon the interior surface 42 of the palmer surface 44 of the glove 40. The extent of the protuberances 52 along the interior surface 42 of the palmer surface 44 of each of the digits is shown. Each pyramidal node 52 is devised to impress into the innervate glabrous ii skin of the palmer of the user's hand when the glove 40 is worn. As with the sock 20 embodiment described above, the elastic properties of the material from which the glove 40 is manufactured may force impression of each node 52 into contact with the user's innervate glabrous skin. Such pressure is increased when the user picks up an object or grasps an object such that the force of contacting the object proportionately increases the pressure applied by focusing the afferent signaling in the manner previously described. The widening of each pyramidal node may therefore increase afferent signaling in increasing proportion to the pressure applied, whereby inurement of the stimulation is preventable in-use of the glove 40. In other words, use of the glove 40 continues varied stimulation of the receptive fields sufficiently to maintain efficacy of mechanoreception, perfusion pressure, and increased blood flow in use of the glove 40.

Figure 15:
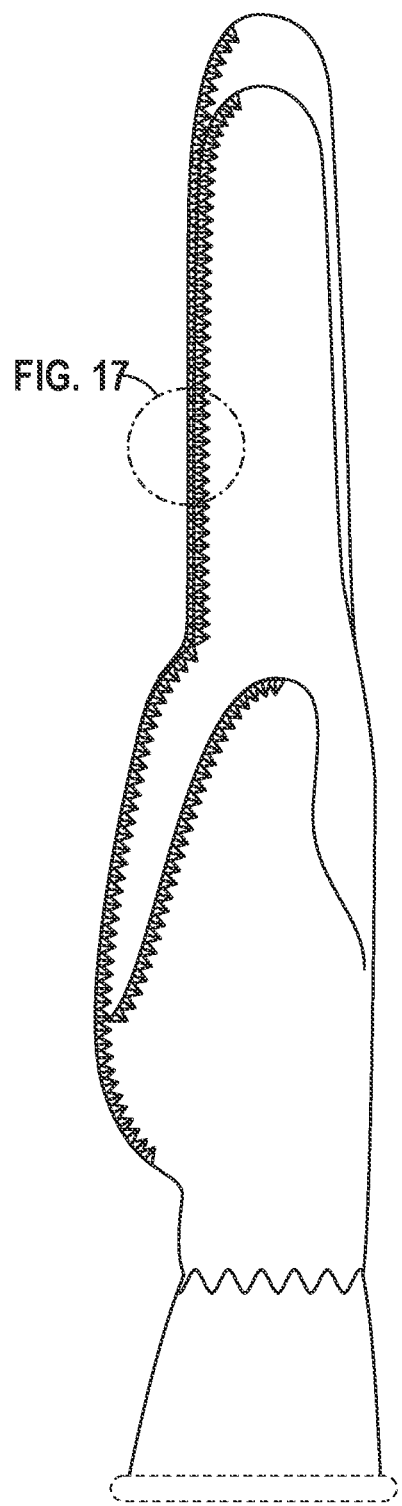
FIG. 15 is a radial side elevation view of an example embodiment of the garment disposed in the form of a glove with side surface rendered transparently to render the interior of the palmer surface of the glove visible for the purposes of illustration.
Figure 16:
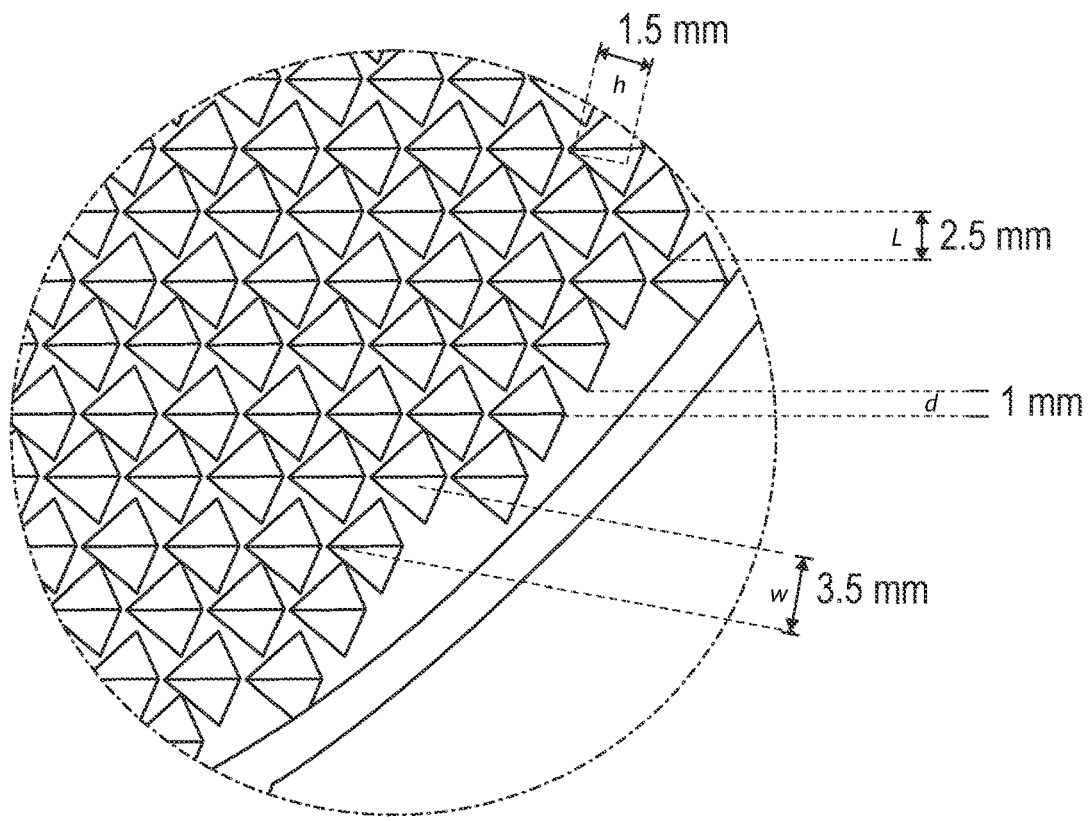
FIG. 16 is a detail view taken from the section shown in FIG. 11.
Figure 17:
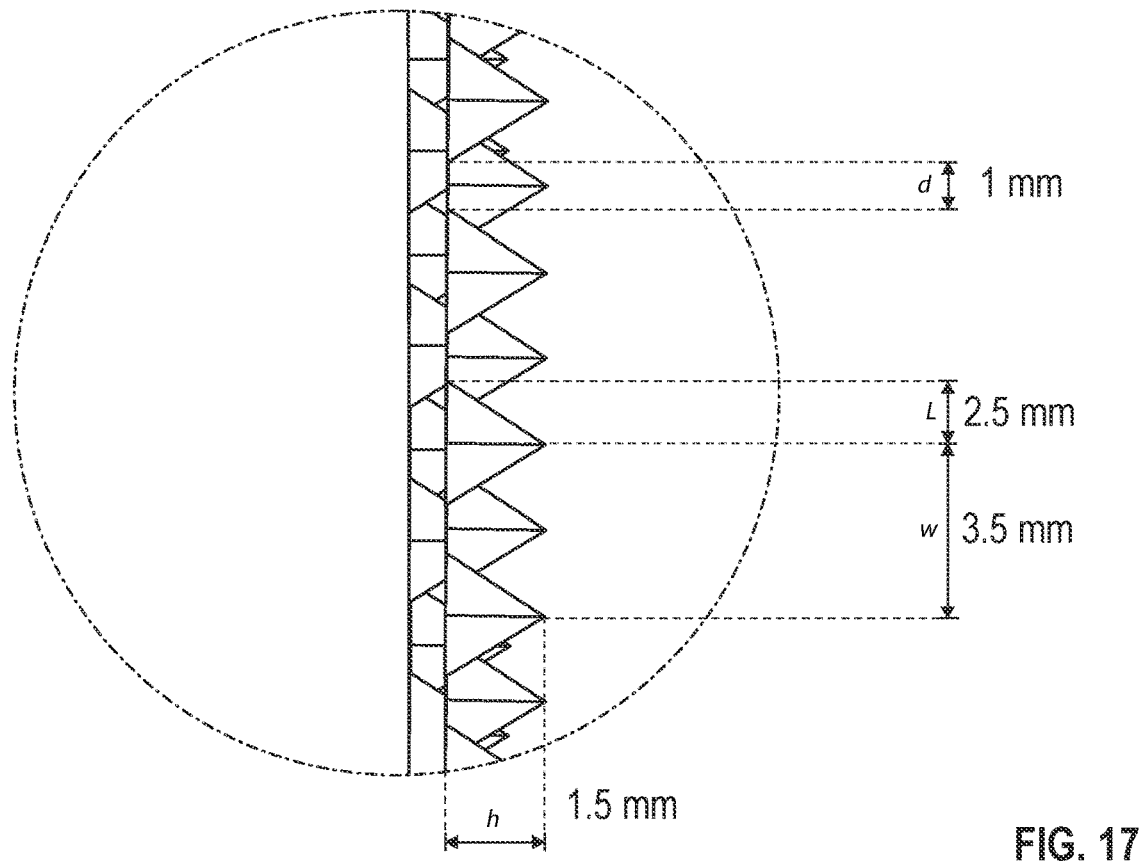
FIG. 17 is a detail view taken from the section shown in FIG. 15.

FIG. 15 is a radial side elevation view of the glove 40 shown transparently for the purposes of illustration of the plurality of protuberances 50. In like manner as has already been described, nodes 52 are shown extending along the interior surface 42 of the palmer surface 44 of the glove 40 extending into each digit, including the thenar of the thumb.

In like manner as shown in FIGS. 9 and 10, FIGS. 16 and 17 are detail views taken from the sections shown in FIGS. 11 and 15 respectively to illustrate the spacing and sizes of each of the pyramidal nodes 52 and the special relationship the nodes 52 occupy as part of the plurality of protuberances 50.

Thus, in all embodiments contemplated herein, the present mechanoreception stimulation garment 10 includes a plurality of protuberances 50 comprising spaced-apart pyramidal nodes 52 disposed upon an interior surface of a garment 10 and configured to target receptive fields in the user's innervate skin.

Additional embodiments are contemplated as within scope of this disclosure, including, for example, sweat bands, hats, garters, belts, tights, stockings, and other garments wearable upon the user in contact with innervate glabrous and, in some embodiments, hairy skin.

What is claimed is:

1. A mechanoreception stimulation garment comprising:
a wearable fabric item of apparel having an interior surface upon which a plurality of protuberances are disposed across the interior surface to contact skin of a user of the item of apparel,
wherein each of said protuberances has a pyramidal shape and is approximately 1.5 mm in height, wherein each of said protuberances has a hardness in the range of approximately Shore A 60 to 80, and wherein the garment is in the form of a sock comprising a sole.

2. The mechanoreception stimulation garment of claim 1 wherein each of the plurality of protuberances is equidistantly spaced in graticulate array and positioned upon the garment to interact with corresponding receptive fields of a foot of a user.

3. The mechanoreception stimulation garment of claim 1, wherein each of the plurality of protuberances comprise an apex and a base.

4. The mechanoreception stimulation garment of claim 1, wherein each base has sides approximately 2.5 mm in length.

5. The mechanoreception stimulation garment of claim 1, wherein each of the plurality of protuberances has a hardness in the range of approximately Shore A 65 to 80.

6. The mechanoreception stimulation garment of claim 4, wherein each of the plurality of protuberances has a hardness in the range of approximately Shore A 65 to 80.

7. The mechanoreception stimulation garment of claim 1, wherein the plurality of protuberances are disposed at least across the interior surface of the sole of the sock corresponding to a metatarsal region of a foot of a user.

8. The mechanoreception stimulation garment of claim 1, wherein the plurality of protuberances are disposed across the entire interior surface of the sole of the sock.

9. The mechanoreception stimulation garment of claim 5, wherein the plurality of protuberances are disposed at least across the interior surface of the sole of the sock corresponding to a metatarsal region of a foot of a user.

10. The mechanoreception stimulation garment of claim 6, wherein the plurality of protuberances are disposed across the interior surface of the sole of the sock.

11. A mechanoreception stimulation garment comprising:
a wearable fabric item of apparel in the form of a glove having an interior surface upon which a plurality of protuberances are disposed across the interior surface to contact skin of a user of the item of apparel, wherein each of the plurality of protuberances has a hardness in the range of approximately Shore A 65 to 80, and wherein each of said protuberances has a pyramidal shape and is approximately 1.5 mm in height, in the form of a glove comprising a palmer surface.

12. The mechanoreception stimulation garment of claim 11, wherein the plurality of protuberances are disposed across the entire interior surface of the palmer surface of the glove.

* * * * *